United States Patent [19]
Yoon et al.

[11] Patent Number: 5,782,844
[45] Date of Patent: Jul. 21, 1998

[54] SUTURE SPRING DEVICE APPLICATOR

[75] Inventors: InBae Yoon, 2101 Highland Ridge Dr., Phoenix, Md. 21131; Samuel C. Yoon, Timonium, Md.

[73] Assignee: InBae Yoon, Phoenix, Md.

[21] Appl. No.: 610,735

[22] Filed: Mar. 5, 1996

[51] Int. Cl.$^6$ ............................................. A61B 17/04
[52] U.S. Cl. ........................... 606/139; 606/142; 606/143
[58] Field of Search .................. 606/139–143; 227/175–182, 901

[56] References Cited

U.S. PATENT DOCUMENTS

| | | |
|---|---|---|
| 816,026 | 3/1906 | Meier . |
| 1,123,290 | 1/1915 | Von Herff . |
| 2,817,339 | 12/1957 | Sullivan . |
| 3,091,828 | 6/1963 | Soltis . |
| 3,446,212 | 5/1969 | Le Roy . |
| 3,545,444 | 12/1970 | Green . |
| 3,604,425 | 9/1971 | Le Roy . |
| 3,716,058 | 2/1973 | Tanner, Jr. . |
| 3,735,762 | 5/1973 | Bryan et al. . |
| 3,870,048 | 3/1975 | Yoon . |
| 3,939,828 | 2/1976 | Mohr et al. . |
| 3,989,049 | 11/1976 | Yoon . |
| 4,217,902 | 8/1980 | March . |
| 4,316,469 | 2/1982 | Kapitanov . |
| 4,337,774 | 7/1982 | Perlin . |
| 4,484,581 | 11/1984 | Martin et al. . |
| 4,485,816 | 12/1984 | Krumme . |
| 4,535,772 | 8/1985 | Sheehan . |
| 4,548,201 | 10/1985 | Yoon . |
| 4,595,007 | 6/1986 | Mericle . |
| 4,637,395 | 1/1987 | Caspar et al. . |
| 4,777,950 | 10/1988 | Kees, Jr. . |
| 4,791,707 | 12/1988 | Tucker . |
| 4,794,927 | 1/1989 | Yoon . |
| 4,869,268 | 9/1989 | Yoon . |
| 4,924,866 | 5/1990 | Yoon . |
| 4,950,258 | 8/1990 | Kawai et al. . |
| 4,961,743 | 10/1990 | Kees, Jr. et al. . |
| 4,979,954 | 12/1990 | Gwathmey et al. . |
| 4,990,152 | 2/1991 | Yoon . |
| 5,007,921 | 4/1991 | Brown . |
| 5,026,379 | 6/1991 | Yoon . |
| 5,026,390 | 6/1991 | Brown . |
| 5,030,224 | 7/1991 | Wright et al. . |
| 5,035,692 | 7/1991 | Lyon et al. . |
| 5,047,047 | 9/1991 | Yoon . |
| 5,053,047 | 10/1991 | Yoon . |
| 5,158,566 | 10/1992 | Pianetti . |
| 5,171,252 | 12/1992 | Friedland . |
| 5,174,276 | 12/1992 | Crockard . |
| 5,207,692 | 5/1993 | Kraus et al. . |
| 5,217,473 | 6/1993 | Yoon . |

(List continued on next page.)

FOREIGN PATENT DOCUMENTS

| | | |
|---|---|---|
| 9505778 | 3/1995 | WIPO . |
| WO96/03925 | 2/1996 | WIPO . |

*Primary Examiner*—Gary Jackson

[57] ABSTRACT

A suture spring device applicator includes a storage portion configured to hold one or more suture spring devices in a substantially relaxed, contracted state and a guide disposed distally of the storage portion to receive a suture spring device in an elastically deformed, expanded state for positioning in or in relation to anatomical tissue. A pusher is used to bias the suture spring device distally so that, when the guide is rotated and moved proximally relative to the suture spring device, the device will be loaded into the guide in the elastically deformed, expanded state. The guide is then positioned in or in relation to anatomical tissue and is retracted or moved proximally relative to the suture spring device which is held in place by the force of the pusher. When the guide is removed, the suture spring device is no longer restrained and can move from the elastically deformed, expanded state toward the substantially relaxed, contracted state to apply a predetermined force to compress the anatomical tissue. The applicator preferably includes a central channel through which instruments, such as tissue penetrating instruments and tissue grasping instruments, can be inserted prior to or during an operative procedure.

38 Claims, 10 Drawing Sheets

U.S. PATENT DOCUMENTS

| | | |
|---|---|---|
| 5,222,976 | 6/1993 | Yoon . |
| 5,226,908 | 7/1993 | Yoon . |
| 5,242,456 | 9/1993 | Nash et al. . |
| 5,309,927 | 5/1994 | Welch . |
| 5,330,503 | 7/1994 | Yoon . |
| 5,334,209 | 8/1994 | Yoon . |
| 5,342,373 | 8/1994 | Stefanchik et al. . |
| 5,356,424 | 10/1994 | Buzerak et al. ............ 606/223 |
| 5,439,457 | 8/1995 | Yoon . |
| 5,476,505 | 12/1995 | Limon . |
| 5,486,187 | 1/1996 | Schenck . |
| 5,499,990 | 3/1996 | Schülken et al. . |
| 5,522,822 | 6/1996 | Phelps et al. ............ 606/143 |
| 5,562,685 | 10/1996 | Mollenauer et al. ............ 606/144 |
| 5,582,616 | 12/1996 | Bolduc et al. ............ 606/143 |

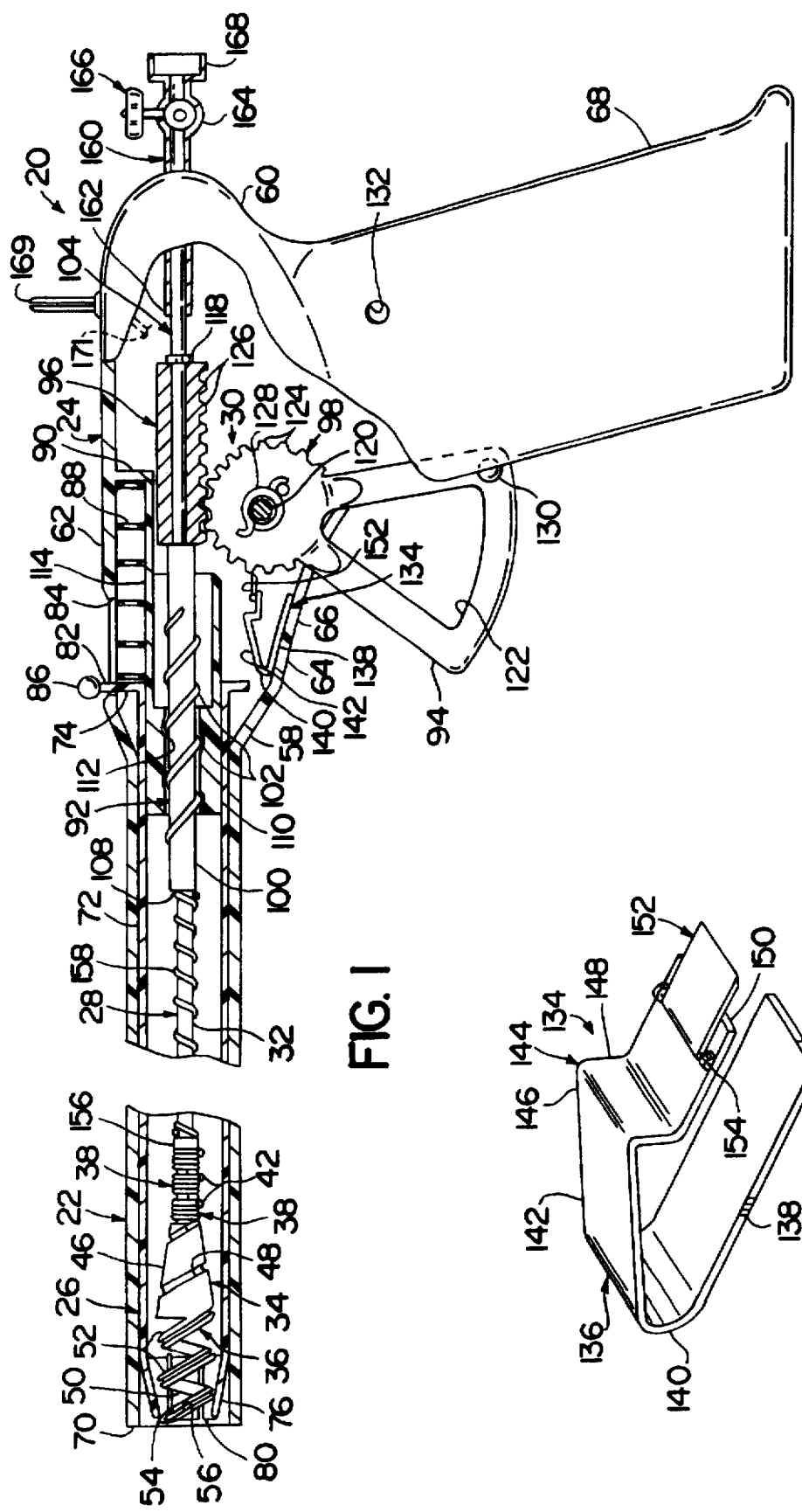

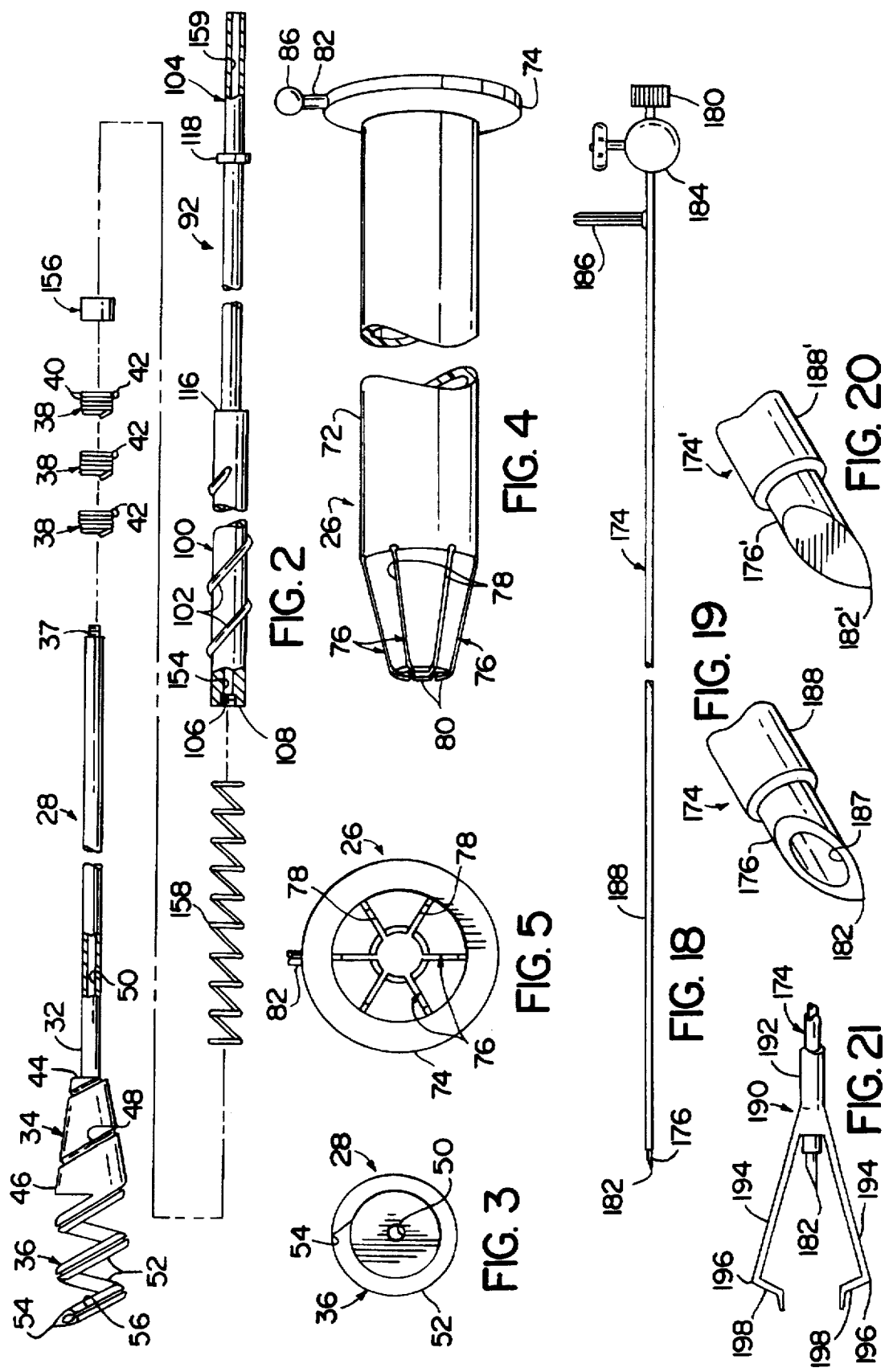

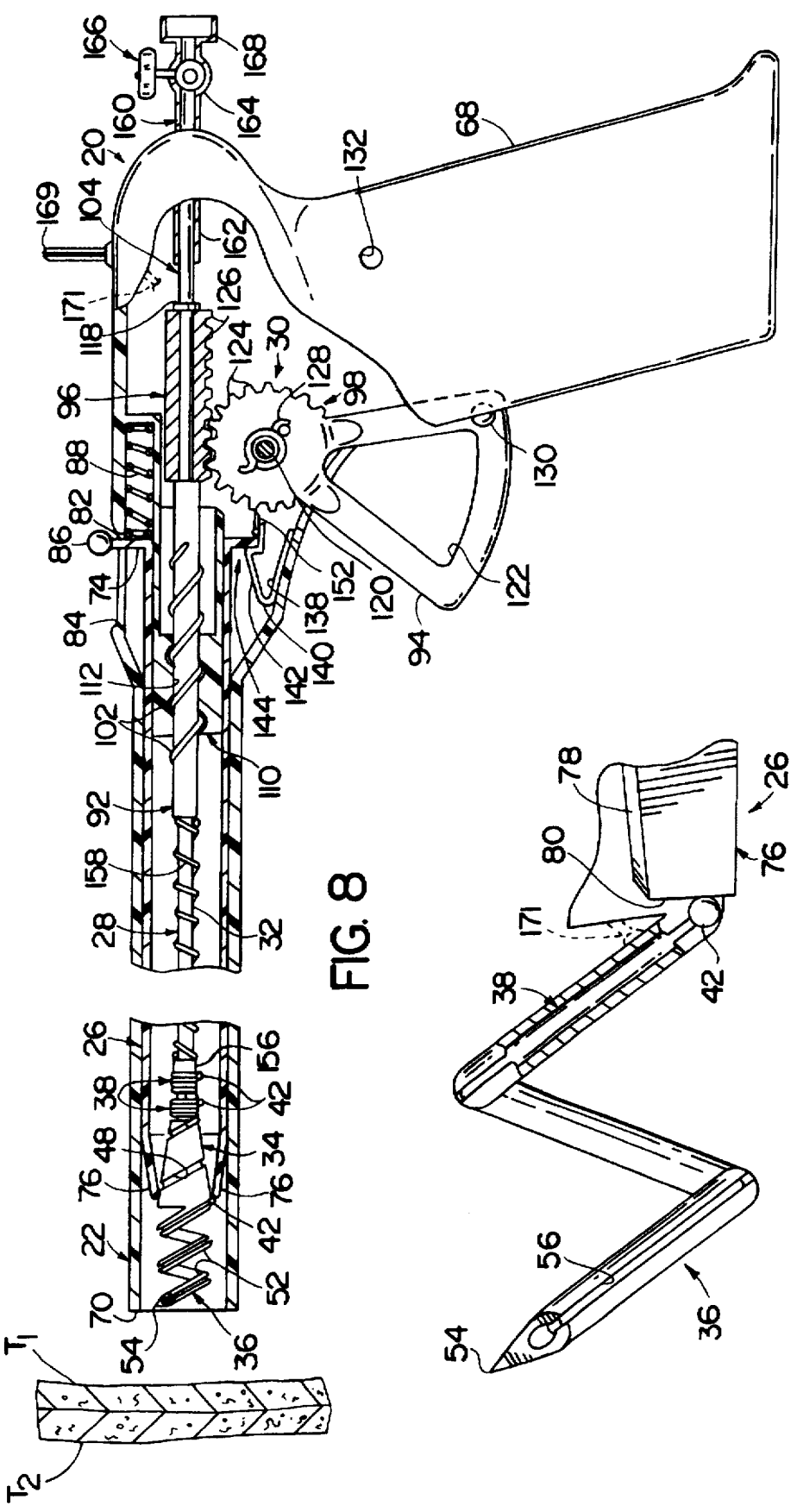

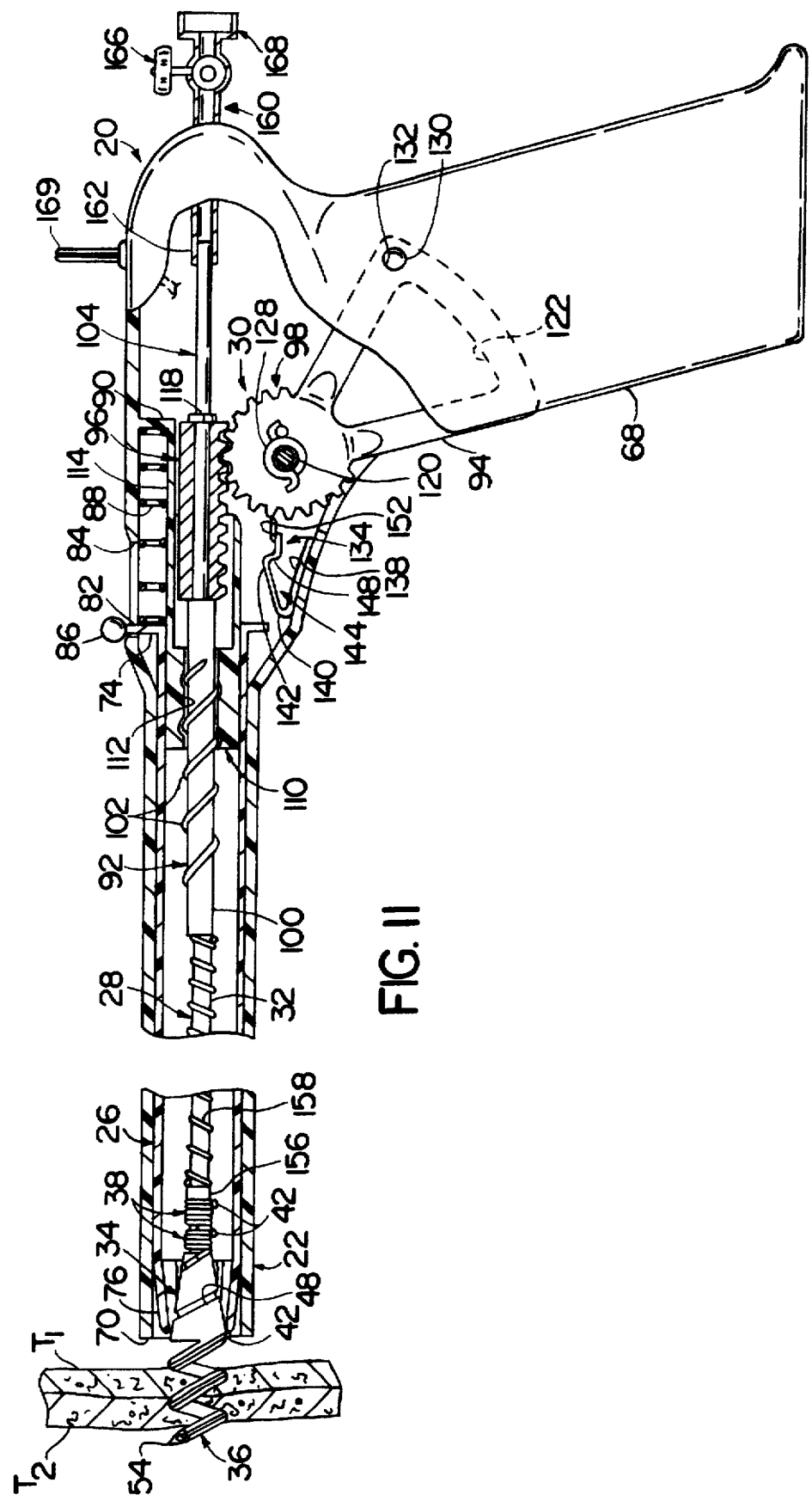

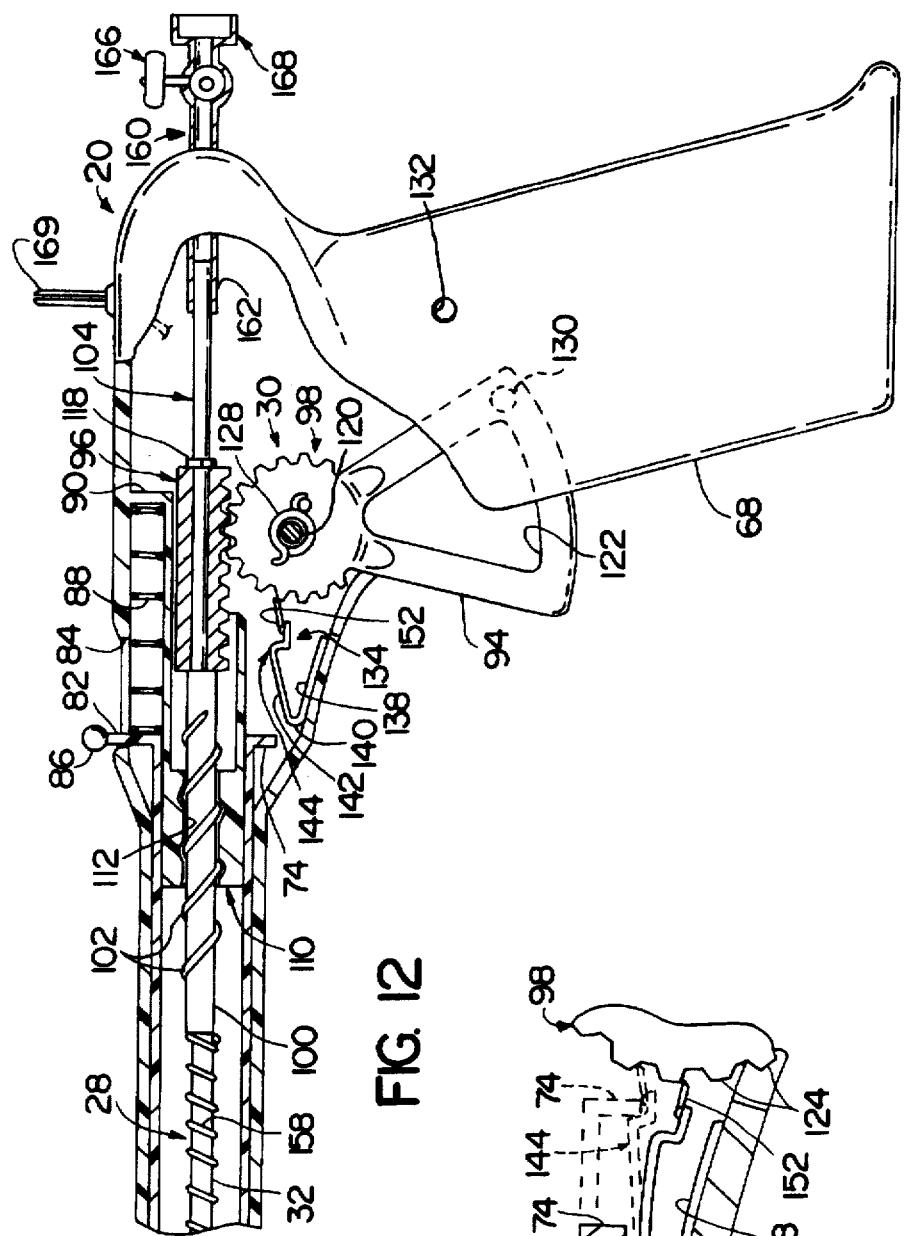

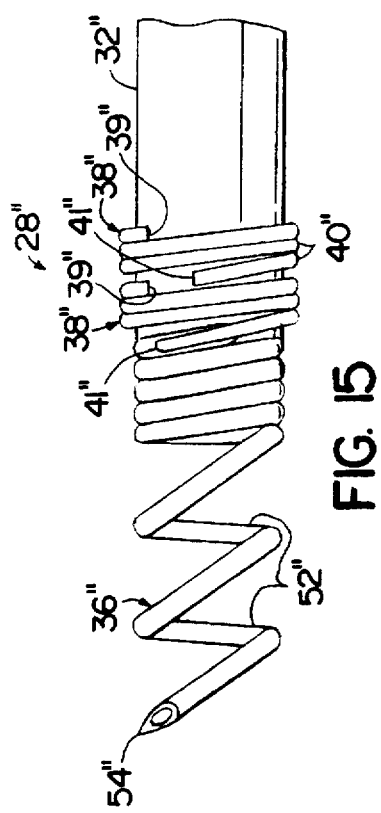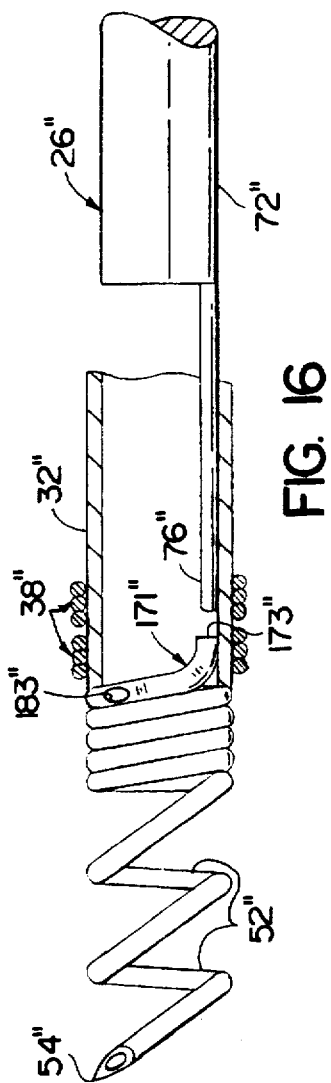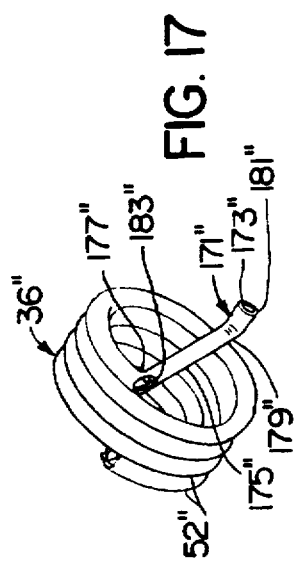

SUTURE SPRING DEVICE APPLICATOR

BACKGROUND OF THE INVENTION

1. Field of the Invention:

The present invention relates to surgical devices and procedures and, more particularly, to a suture spring device applicator, that is, an apparatus for applying at least one suture spring device, for example a suture spring device of the type disclosed in my co-pending patent application Ser. Nos. 08/610 08/610,951, filed concurrently herewith and entitled "Suture Spring Device," the disclosure of which is incorporated herein by reference.

2. Discussion of the Prior Art:

Suturing of bodily tissue is a time consuming part of most surgical procedures including both open surgery and endoscopic or minimally invasive surgery. By "open" surgery is meant surgery wherein the surgeon gains access to the surgical site via a relatively large incision, and by "endoscopic" surgery is meant surgery wherein the surgeon gains access to the surgical site via one or more portals through which endoscopes are introduced to view the surgical site and through which various instruments are introduced to the surgical site. There are many common endoscopic surgical procedures, including arthroscopy, laparoscopy (pelviscopy), gastroentroscopy and laryngobronchoscopy, for example.

In the past, suturing was accomplished with the use of a sharp suture needle attached to the end of a length of suture material. Depending on the size of the suture needle and the type of surgery being performed, the suture needle was either grasped manually or with a needle holding instrument and moved to cause a sharp tip of the needle to penetrate and pass through anatomical tissue. When the sharp tip of the needle emerged from the tissue, the body of the needle was released so that the distal end of the body adjacent the tip could be grasped to pull the needle and the suture material attached to the needle through the tissue. Once the suture material was pulled through the tissue, the surgeon tied a knot in the suture material and adjusted the tension on the suture material to accommodate the particular tissue being sutured and to control approximation, occlusion, attachment or other conditions of the tissue. However, the process of tissue penetration and knotting of the suture material can be time consuming and tedious work, particularly when performed in connection with microsurgery and endoscopic surgery, and can unduly prolong the duration of surgery and therefore the period in which the patient is under anesthesia. Nevertheless, endoscopic surgery is preferred over open surgery due to the greatly reduced trauma and wound healing time for the patient and due to concomitant cost savings associated with shorter hospital stays and performing surgery in non-hospital or out-patient surgery sites.

Accordingly, there has been much effort spent to develop techniques for facilitating the suturing normally performed by use of a suture needle and a length of suture material. One technique, exemplified by U.S. Pat. Nos. 3,545,444 to Green and 4,595,007 to Mericle, employs elongated wire sutures formed of ductile materials that are bent into coiled shapes by a curved tip of a suturing instrument. The wire sutures can be bent around tubular structures or through anatomical tissue and will tend to remain in the bent condition to hold the tissue together; however, once bent, the wire sutures will not compress the tubular structures or tissue so that it is necessary to approximate the tubular structures or tissue prior to or concurrently with bending of the sutures.

The use of stapling instruments has also been proposed, as exemplified by U.S. Pat. Nos. 4,979,954 to Gwathmey et al, 5,465,894 to Clark et al, 5,465,895 to Knodel et al, 5,465,896 to Allen et al, 5,467,991 to Tsuruta et al, 5,480,089 to Blewett and 5,486,187 to Schenck; however, stapling instruments typically include separate staple driving and staple forming or anvil portions for positioning on opposite sides of the tissue to be stapled. This requires access to both sides of the tissue and increases the size of the instruments and the portals through which the instruments are passed in endoscopic procedures. Some stapling instruments do not have a separate anvil portion and are thus capable of applying staples from one side of the tissue; however, the staples must still be formed of a ductile material and bent to a final shape by such instruments requiring relatively complex mechanisms which increase the cost of such instruments. Another disadvantage of stapling instruments is that the staples have sharp, tissue penetrating tips which remain in the tissue after the staples have been bent into their final shape.

Other techniques that have been proposed include electrical coagulation, mechanical devices such as clips and clamps, and lasers; however, no alternative technique has yet been well accepted by surgeons to produce the results obtained by suturing and tying. Thus, there is a great need for suturing techniques useful in endoscopic surgery that permit surgeons to suture anatomical tissue in a time efficient, consistent and precise manner.

SUMMARY OF THE INVENTION

Accordingly, it is a primary object of the present invention to overcome the above-mentioned disadvantages of the prior art and to provide an apparatus and method for applying a suture spring device in or in relation to anatomical tissue.

Another object of the present invention is to use an applicator to position a suture spring device in or in relation to around anatomical tissue in an elastically deformed, expanded state and to allow the suture spring device to move toward a relaxed, contracted state to compress, approximate, occlude, fasten or control other conditions of the anatomical tissue.

A further object of the present invention is to apply a plurality of suture spring devices to anatomical tissue using a suture spring device applicator without having to remove the applicator from the body for reloading.

Some of the advantages of the present invention over the prior art are that procedures such as suturing, ligating and fastening of anatomical tissue can be performed in less time with fewer instruments and with greater consistency, that the suture spring device applicator permits suture spring devices to be applied from one side of the anatomical tissue without the need of having to position or reposition instruments on an opposite side of the tissue, that the suture spring device applicator can apply suture spring devices made of bioabsorbable and non-bioabsorbable materials, that the suture spring device applicator can be adapted for use in endoscopic and non-endoscopic procedures, and that a plurality of suture spring devices can be carried by the suture spring device applicator to permit suture spring devices to be applied at multiple locations within the body without the need of having to withdraw the applicator from the body for reloading.

The present invention is generally characterized in an applicator for applying a suture spring device in relation to anatomical tissue including a storage portion configured to hold at least one suture spring device in a substantially relaxed, contracted state, a guide disposed distally of the storage portion and including a hollow, tubular body configured to receive therein a suture spring device in an elastically deformed, expanded state for positioning in or in relation to anatomical tissue, and a pusher movable in relation to the guide to control the position of a suture spring device relative to the guide. An expander is preferably disposed between the storage portion and the guide to elastically expand the suture spring device as it is moved distally from the storage portion to the guide. The expander can be formed separately or integrally with the guide and can be a tubular extension of the guide or a solid surface with a groove extending from the storage portion to communicate with an opening in the guide. For example, the expander could define a conical surface of increasing diameter in a distal direction with the groove defining a helical path around the conical surface between the storage portion and the guide so that a suture spring device advanced along the groove will be axially and/or radially expanded. The pusher is preferably movable in relation to the guide to engage a suture spring device and can be made to lock in a retracted position behind the suture spring device so that as the guide is moved proximally relative to the suture spring device, the device will be advanced distally or loaded into the guide. The pusher is preferably biased to move distally so that, when the pusher is unlocked, it will continue to engage the suture spring device as the guide is moved distally to be positioned in or in relation to anatomical tissue. The pusher holds the suture spring device substantially stationary as the guide is moved proximally relative to the tissue or removed, thereby allowing the suture spring device to move from the elastically deformed, expanded state toward the relaxed, contracted state in or in relation to the tissue in order to apply a predetermined compressive force thereto. In one embodiment, the pusher includes a tubular body with inwardly biased fingers at a distal end for engaging the suture spring device. In another embodiment, the pusher includes a flexible rod or finger slidingly movable through the hollow, tubular body of the guide.

Yet another aspect of the present invention is generally characterized in an applicator for applying a suture device in or in relation to anatomical tissue including a storage portion configured to hold at least one suture device, a guide disposed distally of the storage portion and including a hollow, tubular body of coiled configuration with a proximal opening to receive a suture device therein, and a pusher movable in relation to the guide to control the position of the suture device in relation to the guide. The pusher can be made to lock in a retracted position behind a suture device so that, if the guide is retracted, the suture device will be advanced distally or loaded into the guide. The pusher is preferably biased to move distally so that, when it is unlocked, the pusher will continue to engage the suture device as the guide is moved distally to be positioned in or in relation to anatomical tissue. The pusher will hold the suture device substantially stationary so that, when the guide is removed, the suture device will remain in or in relation to the anatomical tissue and be allowed to move from the expanded state toward the contracted state.

A further aspect of the present invention is generally characterized in an applicator for applying a suture spring device in or in relation to anatomical tissue including a housing, an outer tubular member having a proximal end mounted by the housing and terminating distally at a distal end, an inner member movably disposed in the outer tubular member and including a storage portion configured to hold at least one suture spring device in a substantially relaxed, contracted state and a guide disposed distally of the storage portion to receive a suture spring device in an elastically deformed, expanded state, a pusher movably disposed in the outer tubular member to engage a suture spring device so that the position of the suture spring device relative to the inner member can be controlled, and a drive mechanism coupled with the inner member to move the inner member relative to the outer tubular member when operated. The applicator can also include a locking mechanism selectively engageable with the pusher to lock the pusher in a retracted position where a distal end of the pusher engages a suture spring device in the storage portion of the applicator so that, when the inner member is moved proximally relative to the pusher, the suture spring device will be advanced distally into the guide. The inner member can be rotated as it is retracted, for example using splines formed on a drive shaft of the drive mechanism. If provided with splines, the drive shaft is rotated as it is advanced to facilitate positioning of the guide and suture spring device disposed therein in or in relation to anatomical tissue. The pusher is unlocked or released when the inner member is moved distally and is preferably biased distally to hold the suture spring device substantially stationary in relation to the anatomical tissue as the guide is retracted or moved proximally so that the suture spring device will move from the elastically deformed, expanded state toward the relaxed, contracted state to apply a predetermined compressive force to the tissue.

Still another aspect of the present invention is generally characterized in a method of applying a suture spring device in relation to anatomical tissue including the steps of storing the suture spring device in a substantially relaxed, contracted state, elastically deforming the suture spring device from the relaxed, contracted state to an elastically deformed, expanded state, loading the suture spring device into a guide in the elastically deformed, expanded state, positioning the suture spring device relative to anatomical tissue in the elastically deformed, expanded state using the guide, and removing the guide to allow the suture spring device to move resiliently from the elastically deformed, expanded state toward the relaxed, contracted state to apply a predetermined compressive force to the tissue. The loading step can, for example, include holding the suture spring device in a substantially stationary position and moving the guide relative to the suture spring device, in which case the guide can be rotated and/or moved proximally relative to the suture spring device. Similarly, the guide can be removed from the suture spring device by holding the suture spring device substantially stationary and moving the guide relative to the suture spring device, for example by rotating and/or moving the guide proximally relative to the suture spring device. In both cases, the suture spring device can be held in a substantially stationary position by positioning a pusher behind the suture spring device and either locking the pusher in place or biasing the pusher distally relative to the guide.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 1 is a broken side view, partly in section, of a suture spring device applicator according to the present invention.

FIG. 2 is an exploded side view, partly in section, of an inner member for the suture spring device applicator according to the present invention.

FIG. 3 is a front view, in elevation, of the inner member of FIG. 2.

FIG. 4 is a side view, in broken longitudinal elevation, of a pusher for the suture spring device applicator according to the present invention.

FIG. 5 is a front view, in elevation, of the pusher shown in FIG. 4.

FIG. 6 is an enlarged perspective view of a pusher locking mechanism for the suture spring device applicator according to the present invention.

FIGS. 7 and 8 are side views, in broken longitudinal elevation, illustrating loading of a suture spring device into the guide of an applicator according to the present invention.

FIG. 9 is an enlarged fragmentary side view, partly in section, of a suture spring device disposed within a guide.

FIG. 10 is a fragmentary side view, partly in section, illustrating operation of the locking mechanism of FIG. 6.

FIGS. 11–13 are side views, in broken longitudinal elevation, illustrating use of the applicator to position a suture spring device in relation to anatomical tissue.

FIG. 15 is a fragmentary side view, in elevation, illustrating a further modification of the inner member according to the present invention.

FIG. 16 is a fragmentary side view, partly in section, of the modified inner member of FIG. 15 showing a modified pusher for use therewith.

FIG. 17 is a fragmentary perspective view of the proximal end of the guide shown in FIGS. 15 and 16.

FIG. 18 is a broken side view, in elevation, of a tissue penetrating instrument for use with the applicator according to the present invention.

FIGS. 19 and 20 are enlarged fragmentary perspective views of modified tissue penetrating tips for the instrument shown in FIG. 18.

FIG. 21 is a fragmentary side view in elevation of a tissue grasping instrument for use with the applicator according to the present invention.

DESCRIPTION OF THE PREFERRED EMBODIMENTS

Figure 7:
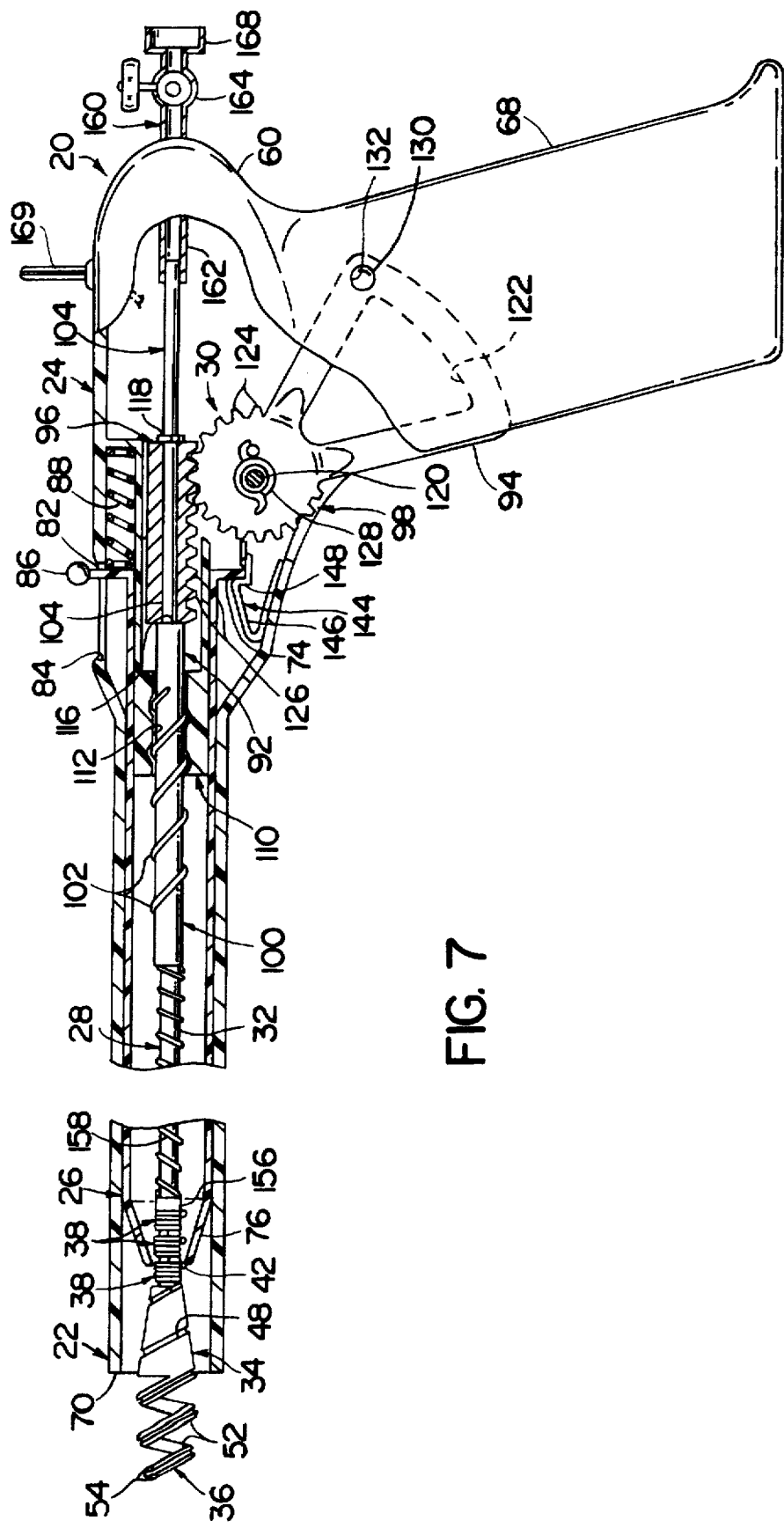

The applicator of the present invention is described hereinafter as an apparatus for applying suture spring devices of coiled configuration such as those described in my aforementioned co-pending patent application Ser. No. 08/610,951, filed concurrently herewith and entitled "Suture Spring Device"; it will be appreciated, however, that the applicator can be used to apply a wide variety of suture devices, including suture devices of coiled and non-coiled configuration which are elastically or plastically deformable or which rigidly maintain a predetermined shape when applied.

A suture spring device applicator 20 according to the present invention, as shown in FIG. 1, includes an outer tubular member 22 extending distally from a housing 24, a middle tubular member or pusher 26 received within the outer tubular member, and an elongate inner member 28 received within the middle tubular member and coupled with a drive mechanism 30 in the housing.

As best seen in FIG. 2, inner member 28 includes an elongate storage portion 32, a frustoconical expander 34 at the distal end of the storage portion and a hollow, tubular guide 36 of coiled configuration extending distally from the expander. Storage portion 32 is shown as an elongate, hollow cylinder with an externally threaded proximal end 37 and an outer diameter of predetermined dimension so that a plurality of centrally apertured suture devices, for example suture spring devices 38, may be received thereon in an unexpanded, relaxed or contracted state in end-to-end series fashion as shown. For purposes of illustration, each of the suture devices is shown as a centrally apertured suture spring device of coiled configuration including an elastic, wire-like body defining a series of connected coils or rings 40 of generally circular configuration, the rings being of like diameter and extending between proximal and distal ends of the elastic body concentric with a longitudinal axis of the device. A knob or handle 42 in the form of a ball is carried on an outer peripheral, convex edge or surface of the body of the suture spring device near the proximal end and extends radially or laterally outward relative to the longitudinal axis of the device. The body of the suture spring device is formed of an elastic or resilient material, that is, a material able to recover its original shape or position after having been deformed. Any medically acceptable bioabsorbable or nonbioabsorbable elastic material can be used for the body of the device including, but not limited to, titanium, nickel-titanium alloys, stainless steel and plastics such as nylon. Further details of suture spring device 38 are set forth in my abovereferenced co-pending application Ser. No. 08/610,951 and several embodiments of suitable suture spring devices are disclosed therein.

Frustoconical expander 34 defines an annular step or shoulder 44 at the distal end of storage portion 32 and a substantially conical surface 46 extending from the shoulder to guide 36. A groove 48 in the conical surface defines a helical path around the expander extending from shoulder 44 at the distal end of the storage portion to guide 36. As best seen in FIGS. 2 and 3, the hollow, cylindrical storage portion and frustoconical expander cooperate to define a central passage or channel 50 along a longitudinal axis of the inner member to permit passage of surgical instruments, anatomical tissue and various types of fluids therethrough.

Guide 36 includes a tubular body 50 of coiled configuration defining a series of connected rings or coils 52 of generally circular configuration terminating at a sharp, tissue penetrating tip 54 at the distal end of the guide. Rings 52 of the guide have a predetermined radius of curvature and a predetermined axial spacing therebetween which are greater than the diameter and axial spacing between rings 40 of the suture spring device in the unexpanded, relaxed state. Rings 52 of the guide are also hollow to define a lumen therethrough in communication with groove 48 in the expander. A slot 56 disposed along an outer peripheral, convex edge of the guide body communicates between an outer surface of the guide and the lumen and is of sufficient size to receive and hold the body of a suture spring device while preferably being V-shaped in transverse cross-section and somewhat narrower in width than the diameter of the suture spring device body to allow knob 42 of the suture spring device to slide along the slot while preventing the body of the device from slipping therethrough. The guide can be made of any suitable medically acceptable material, such as stainless steel, so long as it is configured to have a stiffness suitable for maintaining the suture spring device in an elastically deformed, expanded state.

The helical path defined by groove 48 around the expander communicates with the open proximal end of guide 36 to facilitate loading of a suture spring device into the guide. Because the expander is frustoconically shaped, the diameter of the helical path increases in the direction of the guide so that a suture spring device advanced along the groove will be received by the guide in an elastically deformed, radially expanded state. Alternatively, or in addition to increasing the diameter of the helical path about the expander, the axial spacing of the helical path may be gradually increased in the distal direction so that the suture spring device will be axially expanded as it is advanced along the groove into the guide.

Referring again to FIG. 1, housing 24 includes longitudinally spaced front and rear walls 58 and 60 of rounded configuration, a top wall 62 in configuration parallel to a longitudinal axis of the outer tubular member, and a bottom wall 64 having a concave portion 66 curving downward from the front wall to connect with a handle 68 oriented substantially perpendicular to the longitudinal axis of the outer tubular member.

Outer tubular member 22 is open at both ends and extends from an opening in the housing front wall 58 to terminate distally at a blunt distal end 70. It will be appreciated, however, that distal end 70 of outer tubular member 22 can be tapered or chamfered as desired or have any other suitable distal configuration dependant upon the procedure to be performed. Preferably, the outer tubular member is made of a substantially cylindrical length of a substantially rigid material, such as a medically acceptable plastic or metal material. The outer tubular member and housing can be of integral one-piece construction as shown or can be formed separately and joined together by any suitable method including, but not limited to, threaded engagement, adhesive bonding or friction fit.

Pusher 26 includes a tubular body 72 telescopically fitted within the outer tubular member 22. The tubular body of the pusher terminates proximally at a transverse flange 74 disposed within housing 24 between front and rear walls 58 and 60 of the housing; and, as best seen in FIGS. 4 and 5, a distal end of tubular body 72 is split longitudinally to form a plurality of fingers or flaps 76 which are normally biased radially inward as shown to engage the proximal end of a suture spring device as will be described in greater detail below. Fingers 76 are generally trapezoidal in shape with tapered sides 78 and a flat distal end 80. When biased together as shown in FIG. 4, distal ends of the fingers cooperate to define a generally circular abutment surface of predetermined diameter having a dimension to abut knob 42 of a suture spring device while receiving coils 40 of an adjacent, proximally spaced suture spring device therein. A post 82 extends upwardly from flange 74 of the pusher through a slot 84 formed in the top wall of housing 24 parallel to the longitudinal axis of the instrument and terminates at a knob or handle 86 disposed externally of the housing. Pusher 26 can be formed of any medically acceptable metal or plastic material having sufficient elastic memory to bias the fingers into the normally closed configuration as shown. A bias member 88 is held in compression between flange 74 of the pusher and an inner wall 90 of the housing to bias the pusher distally toward an extended position where post 82 of the pusher abuts the distal end of slot 84 in the housing and distal end 80 of the pusher is disposed adjacent the distal end of outer tubular member 22. Bias member 88 is shown as a helical coil spring but can include various other types of springs as well as other types of bias devices including compression springs, tension springs, torsion springs, pan springs, leaf springs, rubber, plastic or magnets, for example.

Drive mechanism 30 includes a drive shaft 92 coupled with a trigger 94 via a rack 96 and pinon 98. Drive shaft 92 includes a distal portion 100 with splines 102 and a proximal portion 104 carrying the rack. Distal portion 100 is internally threaded at 106 to couple with the proximal end 37 of inner member 28 and is of greater diameter than storage portion 32 to define an annular step or shoulder 108 at the proximal end of the storage portion. A rotator 110 with an internally threaded passage 112 therethrough is mounted at the distal end of a tubular support member 114 disposed within pusher 26 and secured to inner wall 90 to threadedly receive the splined, distal portion of drive shaft 92. Proximal portion 104 of the drive shaft is of smaller diameter than distal portion 100 so that a radial step or shoulder 116 is formed at the intersection thereof, and the rack 96 is disposed between the shoulder and a flange 118 proximally spaced from the shoulder and oriented transverse or perpendicular to a longitudinal axis of the drive shaft.

Rack 96 is generally U-shaped in transverse cross-section with axially spaced teeth 126 defined along a bottom surface of the rack and a slot extending downward, looking at FIG. 1, from an upper surface of the rack. The rack fits under the drive shaft between shoulder 116 and flange 118 with clearance to permit independent rotational movement of the drive shaft within the slot which is at the same time sufficiently narrow to assure that upstanding legs of the rack on opposite sides of the shaft will abut the shoulder and flange to permit axial movement to be transmitted between the rack and the shaft.

Trigger 94 is pivotally mounted on a pin 120 secured to a wall or walls of the housing and is generally triangular in shape with a cut-out or opening 122 formed therethrough to accommodate one or more fingers of the user if desired. Looking at FIG. 1, pinion 98 is disposed concentric with pin 120 at the upper end of trigger 94. The pinion is generally circular with a plurality of circumferentially spaced teeth 124 and a diameter to cause the teeth to mesh with teeth 126 of the rack. A torsion spring 128 is disposed around pin 120 and connected between pinion 98 and housing 24 to bias the trigger in a clockwise direction, looking at FIG. 1. A spring-loaded button 130 is carried at a lower, proximal end of the trigger and is radially aligned with a circular opening 132 in the handle 68 to lock the trigger within the handle in a manually releasable manner when the trigger is depressed or moved counter-clockwise looking at FIG. 1.

As best seen in FIG. 6, a locking mechanism 134 for locking pusher 26 in a retracted position and releasing the pusher to be moved distally by the bias member 88 upon depression of trigger 94 includes a latch or locking spring 136, made of a strip of resilient material, formed to have a substantially flat base 138 secured to the bottom wall 64 of the housing and a bend 140 joining the distal end of the base with an upwardly angled arm 142 spaced from the base. Arm 142 carries or forms a latch 144 having a distal angled latching surface 146 joining a proximal latching surface 148 disposed substantially transverse to the longitudinal axis of the instrument and substantially parallel to the pusher flange 74. Arm 142 has an extension 150 positioned proximally of latch 148 and a releasing member 152 pivotally mounted on a pin 154 secured to an upper surface of the extension. Releasing member 152 extends from pivot pin 154 in a proximal direction to be disposed between teeth 124 of pinion 98. A torsion spring (not shown) is coiled around pin 154 and fixed to releasing member 152 to bias the releasing member clockwise, looking at FIG. 6, such that the releasing member is biased toward extension 150.

Referring again to FIG. 2, a plurality of suture spring devices 38 are received and loaded onto storage portion 32 of the inner member. A cylindrical abutment member 156 is loaded onto storage portion 32 behind the last of the suture spring devices 38. Member 156 is centrally apertured so that it can slide along storage portion 32. A compression spring 158 is coiled around storage portion 32 and is held in compression between abutment member 156 and the annular step or shoulder 108 defined by the drive shaft at the proximal end of the storage portion when the externally threaded proximal portion 37 of the inner member is threaded into the threaded distal portion 106 of drive shaft 92. It will be appreciated that spring 158 biases the abutment member 156 and, thus, suture spring devices 38 distally until a distalmost suture spring device abuts the shoulder 44 formed by the frustoconical expander 34 at the distal end of storage portion 32. Drive shaft 92 defines a central passage or channel 159 along a longitudinal axis of the shaft which is communicated with central channel 50 of inner member 28 when the components are coupled, thereby establishing a continuous central channel through the length of the applicator for passage of additional instruments, tissue and/or fluids. The central channel is communicated with a tubular member 160 having a distal end 162 telescopically receiving the drive shaft within housing 24 and a proximal end 164 disposed externally of the housing to define a valve 166, such as a stop cock valve, and a coupling 168, for example a Luer fitting, disposed proximally of the valve.

As best seen in FIGS. 1 and 9, an electrical connector 169 is mounted on the top wall 62 of the housing and connected via wires 171 with electrically conductive elements of the applicator for performing electrosurgical procedures such as unipolar or bipolar electrical coagulation, for example using guide 36 as a conductive element. It will be appreciated, however, that the position of electrical connector 169 opposite handle 68 is merely exemplary of the many various locations at which an electrical connector can be positioned. Also, inner surfaces of any of the tubular members, such as inner, middle and outer tubular members 28, 26 and 22, can be electrically insulated to permit passage of electrosurgical instruments therethrough as a backup.

In use, applicator 20 is preferably supplied in the rest condition shown in FIG. 1 with trigger 94 protruding distally from handle 68 in an unlocked position. Pinion 98 at the end of trigger 94 engages a distal end of rack 96 which is biased proximally toward a retracted position by the clockwise rotational bias of the torsion spring acting on the pinion. Rack 96 engages flange 118 to bias drive shaft 92 and inner member 28 to a retracted position where guide 36 is disposed within outer tubular member 22 to protect the sharp tip of the guide. Pusher 26 is unlocked in the rest condition and biased distally toward an extended position where knob 86 abuts a distal end of slot 84 and fingers 76 at the distal end of the pusher engage the guide. Flange 74 at the proximal end of the pusher is distally spaced from latch 144 of locking mechanism 134 when the pusher is in the extended position. As mentioned previously, suture spring devices 38 are held on the storage portion of inner member 28 in an unexpanded, relaxed state. Compression spring 158 pushes abutment member 156 forward in a distal direction into abutting relation the proximalmost suture spring device which, in turn, is pushed distally into the next suture spring device until the distalmost suture spring device abuts shoulder 44 at the distal end of storage portion 32.

A suture spring device 38 is loaded into guide 36 by locking pusher 26 in a retracted position where fingers 76 engage knob 42 of the suture spring device and retracting inner member 28 proximally relative to the suture spring device while maintaining the pusher in the locked position. Referring to FIG. 7, inner member 28 is moved to an extended position by depressing trigger 94 into handle 68 to cause pinion 98 to rotate counterclockwise about pin 120, looking at FIG. 7, thereby forcing rack 96 to move in a distal direction. Rack 96 pushes against shoulder 116 of the drive shaft, forcing the drive shaft to move distally through block 110 which rotates the shaft in a clockwise direction looking distally. Inner member 28 is also moved distally to an extended position where guide 36 is disposed distally of outer tubular member 22. When trigger 94 is completely depressed as shown, button 130 in the trigger will be aligned with opening 132 in the handle and will thus be able to spring outwardly of the trigger into the opening to lock the trigger in the depressed condition. Pusher 26 is then retracted to engage a suture spring device 38 by pulling handle 86 rearwardly or in a proximal direction against the distal bias of bias member 88 to force flange 74 against arm 146 of the locking mechanism. Arm 146 is pushed downwardly by flange 74 as handle 86 is drawn back, allowing the flange to slide over latch 144. When flange 74 is disposed proximally of the latch, arm 142 will spring upwardly positioning proximal latching surface 148 in front of the flange. When handle 86 is released, bias member 88 will bias flange 74 distally into contact with the proximal latching surface which prevents the flange from moving further distally. As the handle is drawn back, fingers 76 at the distal end of the pusher slide along the periphery of inner member 28 and over the suture spring device 38 until they are positioned immediately behind knob 42 of the distalmost suture spring device. Since fingers 76 are biased radially inward, distal ends of the fingers will abut the knob and prevent the knob from moving proximally past the fingers.

Referring now to FIG. 8, pusher 26 is maintained in a locked position with fingers 76 engaging knob 42 at the proximal end of suture spring device 38, and button 130 is depressed to permit trigger 94 to be moved in a clockwise direction about pin 120 under the influence of torsion spring 128. Clockwise movement of the trigger causes pinion 98 to move in a clockwise direction thereby forcing rack 96 to move proximally toward the retracted position. Proximal movement of rack 96 causes drive shaft 92 to move proximally through block 110 which rotates the shaft in a counterclockwise direction looking distally. Inner member 28 retracts with drive shaft 92 and is rotated in the same direction. Suture spring device 38 is prevented from moving proximally by pusher 26 and will thus be received in and expand along the groove 48 in the expander and be loaded or fed into guide 36 as shown in FIG. 9. In the loaded position shown, suture spring device 38 is held in an elastically deformed, expanded state within guide 36, and knob 42 at the proximal end of the suture spring device is aligned with and made to slide along slot 56 in the guide.

With suture spring device 38 loaded within guide 36 as shown in FIGS. 8 and 9, applicator 20 can be used to suture and/or ligate anatomical tissue within the body as described in my aforementioned co-pending application Ser. No. 08/610,951 entitled "Suture Spring Device" and my co-pending application Ser. No.08/610,952 filed concurrently herewith and entitled "Method Of Ligating Anatomical Tissue With A Suture Spring Device," the disclosure of which is incorporated herein by reference. For purposes of illustration, suturing of layered tissue structures $T_1$ and $T_2$ will be described; it being understood that the applicator can be used in a similar fashion to suture other types of tissue and/or to ligate tissue within the body using a suture spring device.

Referring still to FIG. 8, distal end 70 of outer tubular member 22 is positioned adjacent the tissue to be sutured while trigger 94 is depressed. As shown in FIG. 11, depression of trigger 94 into handle 68 causes pinion 98 to rotate in a counterclockwise direction about pin 120. Rack 96 is moved distally by counterclockwise rotation of the pinion causing drive shaft 92 to be moved distally through block 110 and rotated in a clockwise direction looking distally along the longitudinal axis of the applicator. Counterclockwise rotation of pinion 98 also causes teeth 124 of the pinion to press downwardly against releasing member 152 at the proximal end of extension 150 as shown in FIG. 10, causing arm 142 of the locking mechanism to be moved downwardly toward base 138. Downward movement of arm 142 causes latch 144 to move away from flange 74 of pusher 26 allowing the pusher to be moved in the distal direction under the influence of bias member 88. Inner member 28 moves distally and is rotated with drive shaft 92 causing sharp tip 54 of the guide to penetrate into the proximal tissue structure $T_1$. As inner member 28 is moved further distally and rotated, guide 36 will penetrate through anatomical structures $T_1$ and $T_2$ like a corkscrew thereby establishing a helical path through the structures as shown in FIG. 11. Pusher 26 is biased distally under the influence of bias member 88 and will thus maintain contact with knob 42 at the proximal end of suture spring device 38 to assure retention of the device within the guide as it penetrates into the tissue.

Figure 13:
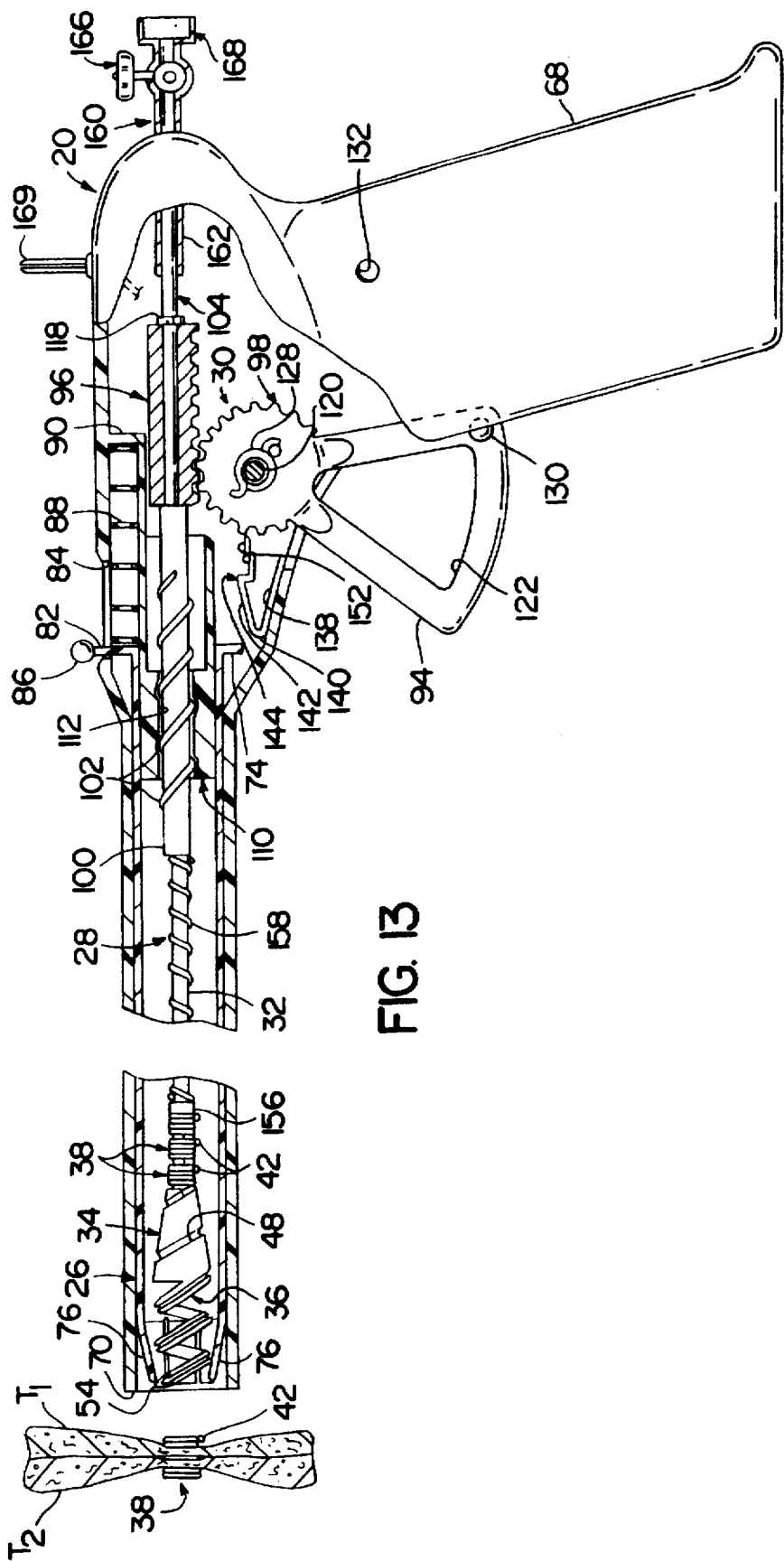

Penetration is complete when trigger 94 is fully depressed within handle 68 and button 130 is engaged within opening 132 of the handle. Guide 36 holds suture spring device 38 in the elastically deformed, expanded state for positioning in or in relation to the anatomical tissue and is removed from the suture spring device by pressing button 132 into opening 130 to allow the trigger to be moved in the clockwise direction under the force of torsion spring 128 as shown in FIG. 12. As trigger 94 moves clockwise about pin 120, rack 96 is moved proximally once more, causing drive shaft 92 to be moved proximally through rotator block 110 and rotated in a counterclockwise direction looking distally along the longitudinal axis of the applicator. Proximal movement of suture spring device 38 is prevented by engagement of fingers 76 with the knob 42 at the proximal end of the suture spring device. Guide 36 is thus unthreaded or removed from suture spring device 38 with knob 42 sliding along slot 56 in the guide to permit the guide to move proximally relative to the suture spring device. As the guide is removed, rings 40 of the suture spring device move from the elastically deformed, expanded condition toward their original relaxed, contracted condition. When guide 36 is removed entirely from suture spring device 38, as shown in FIG. 13, rings 40 of the suture spring device will engage tissue structures $T_1$ and $T_2$ disposed between the coils and exert a predetermined axially compressive force to approximate the tissue structures. It will be appreciated that suture spring devices 38 remaining in applicator 20 are biased distally by compression spring 28 and are thus positioned for loading and use in the manner described above without the need of having to remove the applicator from the body for reloading.

Figure 14:
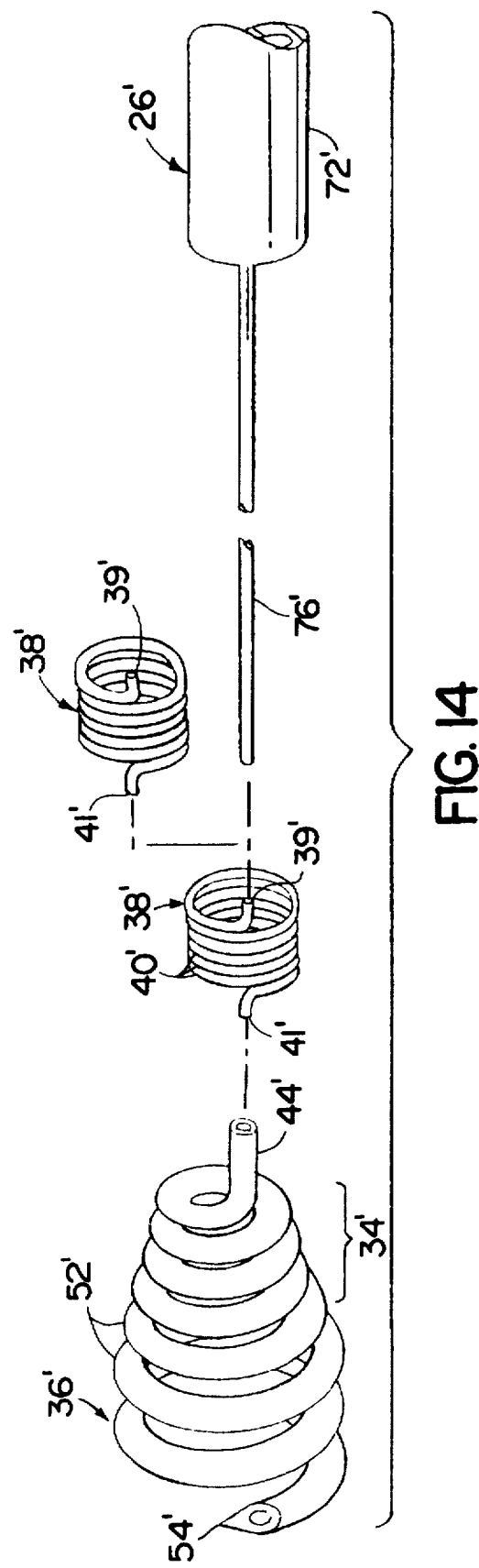
FIG. 14 is an exploded perspective view illustrating a modification of the inner member and pusher according to the present invention.

While the applicator according to the present invention has been described as applying a particular suture spring device, it will be appreciated that the applicator can be adapted to apply a variety of different types of suture spring devices. In FIG. 14, for example, a modified guide 36' and pusher 26' are shown for applying one or more suture spring devices 38' similar to the suture spring devices previously described but without knobs. Each suture spring device 38' includes an elastic body of coiled configuration defining a plurality of rings or coils 40' extending between proximal and distal ends 39' and 41' of the device. Proximal and distal ends 39' and 41' are bent at an angle relative to the coils and extend in axially opposed directions along a longitudinal axis of the device. Tubular guide 36' is similar to the guide previously described but does not include a slot. A proximal end 44' of the guide is bent at an angle relative to rings or coils 52' of the guide to extend along a longitudinal axis of the guide and to be axially aligned with the distal end 41' of the suture spring device 38'. Rings 52' of the guide are of increasing diameter in a distal direction so that the guide will function to elastically deform the suture spring device as it is loaded into the guide, thereby obviating the need for a separate expander. Pusher 26' includes an elastic rod or finger 76' extending distally from a peripheral edge of tubular body 72' in axial alignment with proximal end 39' of suture spring device 38'. The finger 76' has a configuration to fit conformably within and to move or slide along the guide. In use, finger 76' of pusher 26' is aligned with and made to abut proximal end 39' of suture spring device 38' in order to move the suture spring device in the distal direction relative to guide 36'. If more than one suture spring device 38' is disposed within the applicator, the suture spring devices can be loaded in end-to-end series fashion as indicated in FIG. 14 by the presence of the second suture spring device which can be inserted between the distalmost suture spring device and the pusher. The distalmost suture spring device is loaded into the guide in the manner described above, for example by using the pusher to hold the suture spring device in place while the guide is retracted. As the suture spring device is loaded, finger 76' will enter the proximal end 44' of the guide and be elastically deformed within the guide in order to maintain contact with the proximal end 39' of the suture spring device. As the suture spring device 38' is advanced distally through guide 36', it will be elastically deformed by the coils of the guide and will be held in the elastically deformed, expanded state as the guide is positioned in or in relation to anatomical tissue. Once the guide is positioned, the suture spring device is held in a substantially stationary position in relation to anatomical tissue by the finger of the pusher while the guide is removed by sliding along the finger of the pusher in a proximal direction.

Another modification of the applicator according to the present invention, shown in FIGS. 15–17, includes an inner member 28" having a hollow storage portion 32" of cylindrical configuration, a hollow, tubular guide 36" of coiled configuration with a proximal portion 171" extending into the interior of the storage portion and a pusher 26" similar to that shown in FIG. 14, having a hollow, tubular body 72" slidably received within storage portion 32" and an elastic rod or finger 76" extending distally from a peripheral edge of the tubular body to be axially aligned with an open proximal end 173" of the guide. As best seen in FIG. 17, proximal portion 171" includes a first tubular extension 175" extending radially inward from a first bend 177" in the proximalmost coil to a second bend 179" connecting the first tubular extension with a second tubular extension 181" disposed along the interior of storage portion 32" in axial alignment with finger 76". The second tubular extension terminates proximally at open proximal end 173". Storage portion 32" is received telescopically within the longitudinal passage defined by rings 52" of the guide and can be connected thereto in any suitable manner including, but not limited to, adhesive bonding and friction fit. An opening 183" is formed in an outer peripheral, convex surface of the guide adjacent bend 51" and is configured to receive the distal end 41" of a suture spring device, for example suture spring device 38", carried on an outer surface of the cylindrical storage portion. A plurality of suture spring devices 38" are shown, each being similar to suture spring device 38 but without knobs or handles. The suture spring devices are preferably biased distally relative to the guide so that, when the guide is rotated relative to the distalmost suture spring device as described above, the device will be loaded into the guide. Pusher 26" is movable through the tubular body of the guide to control movement of the suture spring device relative to the guide once the device is within the guide; and, it will be appreciated that the finger of the pusher can be used to prevent subsequent suture spring devices 38" from being loaded into the guide by blocking opening 183" when advanced distally beyond the opening to push the suture spring device already loaded within the guide. However, under certain circumstances it may be desirable to have more than one suture spring device disposed within a guide, in which case subsequently loaded suture spring devices will be disposed between the pusher and the distalmost suture spring device, for example in the additional rings 52" at the proximal end of the guide, and the additional devices can be used to push the distalmost device in relation to the guide.

FIGS. 18 and 19 show a penetrating instrument 174 which can be assembled as part of the applicator 20 or inserted through the central channel of the applicator by the user during an operative procedure. The instrument 174 includes an elongate, tubular body 176 having an outer diameter of predetermined dimension to fit within the central channel of the applicator and a length to protrude distally beyond the tip 54 of the guide when fully inserted. Body 176 defines a lumen 187 which extends from a conventional coupling 180, such as a Luer fitting, at a proximal end of the body to a sharp, tissue penetrating tip 182 at a distal end of the body. A valve 184, for example a stopcock valve, is disposed near the coupling at the proximal end of the body and communicated with the lumen to control passage of instruments, fluids and/or tissue through the lumen. An electrical connector 186 protrudes perpendicularly from the body of the penetrating instrument through an electrically insulative layer 188 which is formed about the periphery of the body and made to extend all or substantially all of the length of the instrument to facilitate use of the tip of the instrument for electrosurgical procedures. It will be appreciated that instrument 174 can also be used to penetrate and dissect anatomical tissue, to perform irrigating and aspirating functions, and to administer medicaments to the operative site.

A modification of the penetrating instrument is shown in FIG. 20 wherein the modified penetrating instrument 174' includes an elongate, solid body 176' terminating at a sharp, tissue penetrating tip 182' which can, for example, be used to penetrate and dissect anatomical tissue as well as for electrosurgical procedures.

Another instrument usable with the applicator 20 according to the present invention, as shown in FIG. 21, includes an elongate body 192 terminating distally in a pair of arms 194. Each arm extends distally from the body to a bend 196 connecting the arm with a tissue engaging tip or pincer 198 oriented substantially perpendicular or transverse to the arm. Arms 194 are angularly spaced from one another in opposed relation and are normally biased apart as shown with a gap or spacing between the arms increasing in a distal direction. Tips 198 extend toward one another from the arms in opposed relation and can have any configuration useful for grasping tissue and medical devices. The grasping instrument 190 is preferably formed of an elastic material so that arms 194 and tips 196 can be straightened to pass thru the central channel of the applicator, for example by advancing a tubular sleeve (not shown) distally relative to the arms and inserting the sleeve through the channel with the arms disposed therein. When the distal end of the sleeve protrudes beyond the guide, the sleeve is retracted to allow arms 194 to spread apart as shown. Arms 194 can be drawn together to grasp anatomical tissue and/or devices disposed between the arms by advancing a sleeve distally relative to the arms and/or by moving the instrument proximally relative to the guide. The grasping instrument can be formed with more than two arms, for example to grab weakened portions of anatomical tissue. Body 192 of the tissue grasping instrument 190 can be of hollow, cylindrical configuration as shown or have any other solid or hollow configuration as desired. If hollow, the body of the instrument can be used to allow passage of tissue or fluids therethrough or to accommodate other instruments, such as the penetrating instruments described above.

Figure 22:
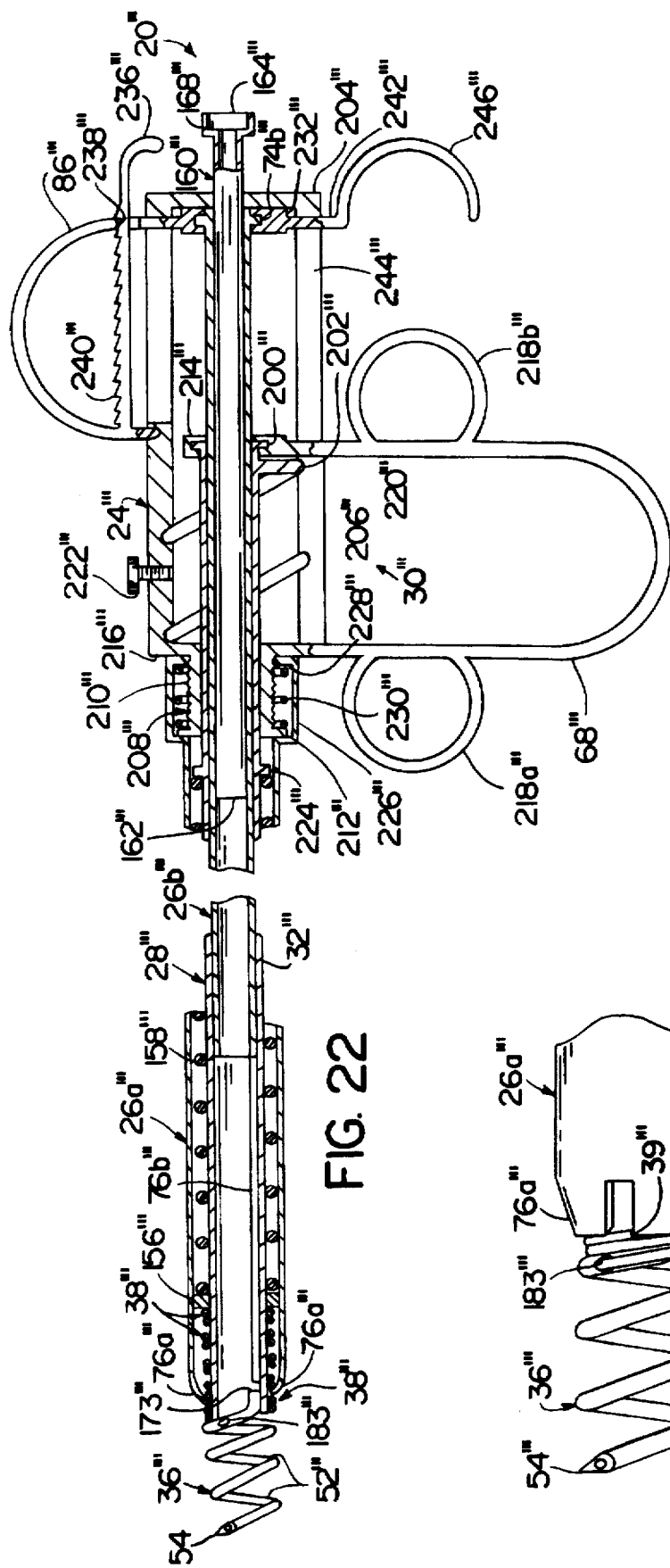
FIG. 22 is a broken side view, partly in section, illustrating a modified applicator according to the present invention.

Another modification of the applicator according to the present invention, shown in FIG. 22 at 20''', is similar to applicator 20 but is shown without a protective outer tubular member. The modified applicator includes a housing 24''', a first pusher 26a''' of tubular configuration extending distally from the housing, and the elongate inner member 28''' received within the first pusher and coupled with a drive mechanism 30''' in the housing, and a second pusher 26b''' received within the inner member and coupled with a handle 86'''. Inner member 28''' includes a hollow tubular storage portion 32''' of cylindrical configuration extending between a transverse proximal flange 200''' disposed within housing 24''' and a guide 36''' similar to guide 36" but with fewer rings 52''' to accommodate a single suture spring device. An outwardly protruding peg, post or pin 202''' extends perpendicularly from a proximal end of storage portion 32''' adjacent flange 200'''. Housing 24''' includes a proximal cylindrical portion 204''' which is internally threaded, grooved or splined at 206''' to receive pin 202''' of the storage member, and a distal cylindrical portion 208''' of smaller diameter than the proximal portion which is externally threaded at 210''' and which terminates distally at an outwardly protruding transverse flange 212'''. Transverse proximal flange 200''' of storage portion 32''' is freely rotatably received within a circular or ring-like collar 214''', and a generally U-shaped handle 68''' is connected between the collar and a forward wall 216''' of housing portion 204''' to bias the inner member proximally relative to the housing. Handle 68''' extends through a slot 220''' formed in the bottom wall of housing portion 204''' parallel to a longitudinal axis of the inner member to connect with collar 214''' and is preferably formed as an integral one-piece unit from an elastic material, such as spring steel, but can be made of other materials and/or be made of separate, pivotally connected pieces which are biased apart. A pair of finger loops 218a''' and 218b''' of generally circular configuration are preferably provided on opposite sides of the handle to accommodate one or more fingers of the user and to permit expansive forces to be applied to the handle if required. A lock 222''' is threadedly mounted on the top of housing portion 204''' and is manually rotatable through the housing to be disposed proximally of collar 214''' when the collar is in an extended position adjacent forward wall 216'''. The lock prevents proximal movement of the inner member, thereby holding the guide at the distal end of the inner member in an extended position as will described further below.

A plurality of suture spring devices, for example suture springs devices 38''', are received on storage member 32''' in a relaxed, unexpanded state and are biased distally in the direction of guide 36'" by a spring 158'" held in compression between a flange or shoulder 224'" on an intermediate section of storage member 32'" and an abutment member 156'" slidably disposed behind the suture spring devices. Suture spring devices 38'" are similar to suture spring devices 38" in that they do not carry a knob or handle, but differ in that they are shown with only two rings. When biased distally, distal end 41'" of the distalmost suture spring device will be longitudinally or axially aligned with opening 183'" in the guide.

Outer, tubular pusher 26a'" extends from a cylindrical hub 226'" at a proximal end to a plurality of inwardly biased fingers 76a'" at a distal end. With pusher 26a'" in the retracted position shown, at least one of the fingers will extend through the space between suture spring devices to contact storage portion 32'" immediately adjacent or behind the proximal end 39'" of the distalmost suture spring device.

Cylindrical hub 226'" terminates proximally in an inwardly protruding transverse flange 228'" which is internally threaded to couple with the externally threaded distal housing portion 208'". Hub 226'" is rotatable about housing portion 208'" to move pusher 26a'" distally relative to the housing while at the same time rotating the pusher, and thus the distalmost suture spring device, about a longitudinal axis of the housing. When pusher 26a'" is in an extended position or condition, inwardly I protruding flange 228'" of the hub will abut outwardly protruding flange 212'" of the housing to prevent further distal movement of the pusher. The threaded length of housing portion 208'" and of hub 226'" can be varied to obtain a desired position for the distal end of the pusher in the extended position. For example, the distal end of the pusher can be made to protrude distally beyond the guide when extended if it is desirable to protect the tip of the guide, for example when passing the applicator through an endoscopic sleeve or portal with internal components that can be damaged by the sharp tip of the guide. A spring 230'" can be held in compression between flanges 212'" and 228'" if desired to bias the hub proximally relative to the housing in order to reduce play in the hub and to prevent the hub from being inadvertently rotated.

The second, inner pusher 26b'" includes a hollow, tubular body 72'" extending from a proximal flange 74b'" disposed in housing portion 204'" to a flexible rod or finger 76b'" mounted on a peripheral edge at the distal end of the tubular body in axial alignment with the open proximal end 173'" of guide 36'". Proximal flange 74b'" is received within a hollow ring or collar 232'" which is connected to one leg of an elastic, U-shaped handle 86'" similar to handle 68'". Handle 86'" extends upwardly, looking at FIG. 22, from collar 232'" through a slot 234'" in the upper wall of the housing and turns downwardly to connect with housing portion 204'" to bias the collar, and thus the pusher, proximally relative to the housing toward a retracted position where a distal end of finger 76b'" is slightly proximally spaced from proximal end 173'" of guide 36'". The handle includes a locking member 236'" which extends longitudinally between legs of the handle and passes through an opening 238'" in the proximal leg. The locking member is biased upwardly, looking at FIG. 22, and has teeth 240'" on an upper surface thereof that engage an upper edge of the opening 238'" to lock the handle in any position and state of compression or expansion. A handle extension 242'" extends downwardly, looking at FIG. 22, from collar 232'" through a slot 244'" in the bottom wall of the housing to terminate at a semi-circular finger loop 246'" having a concave portion axially aligned with and facing finger loops 218a'" and 218b'" of handle 68'".

It will be appreciated that since storage portion 32'" and pusher 26b'" disposed therein are hollow, a central channel is defined through the applicator, for example to be communicated with a tubular member 160'" having a distal end 162'" disposed in the hollow, tubular body of pusher 26b'" and a proximal end 164'" disposed externally of the housing to mount with a coupling 168'", such as a Luer fitting.

Figure 23:
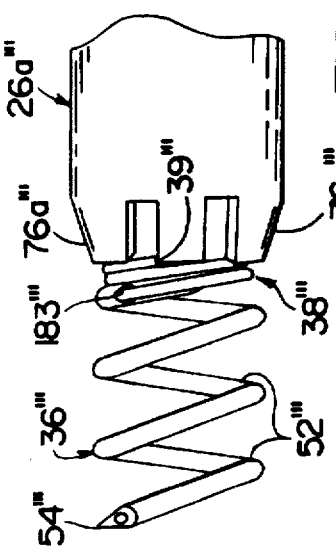
FIG. 23 is an enlarged, fragmentary side view, partly in section, of the distal end of the applicator shown in FIG. 22.

To load a suture spring device 38'" into guide 36'", the suture spring device is advanced distally relative to the guide and rotated in a clockwise direction, looking distally, by grasping hub 226'" at the proximal end of outer pusher 26a'" and by rotating the hub in the clockwise direction. Hub 226'" moves distally as it is rotated, causing pusher 26a'" and fingers 76a'" at the distal end of the pusher to rotate and move distally as well. As mentioned above, in the retracted position, at least one finger 76a'" is disposed adjacent to or behind proximal end 39'" of the distalmost suture spring device 38'" so that as the hub is rotated, the finger adjacent the suture spring device will bear against the proximal end of the device to advance the device distally toward guide 36'" while at the same time rotating the device. As suture spring device 38'" is advanced, distal end 41'" of the device will become aligned with opening 183'" in the guide and will pass through the opening into the interior of the guide as shown in FIG. 23. Finger 76a'" will continue to push suture spring device 38'" into the guide until proximal end 39'" of the device passes through opening 183'", after which the outer pusher will no longer engage the device.

Guide 36'" can then be positioned in or in relation to anatomical tissue or, if the suture spring device 38'" is proximally spaced from the distal end of the guide, the suture spring device can be advanced further distally within the guide to be disposed adjacent the distal end.

To position guide 36'" in or in relation to anatomical tissue, distal tip 54'" of the guide is moved to a position adjacent the anatomical tissue and handle 68'" squeezed or compressed to move collar 214'", and thus flange 200'" of the inner member, distally relative to housing 24'", thereby driving pin 202'" on the inner member along threads or grooves 206'" formed in the housing to rotate and move the inner member distally relative to the tissue. Guide 36'" is mounted at the distal end of inner member 28'" and is thus moved with the inner member to be positioned in or in relation to the anatomical tissue with the suture spring device disposed therein in an elastically deformed, expanded state as described above. If the suture spring device is proximally spaced from the distal end of the guide, inner member 28'" can be locked in place relative to the anatomical tissue by deploying locking member 222'" in the housing to form a proximal abutment surface behind collar 214'" of the handle. Inner pusher 26b'" may then be operated to move finger 76b'" distally into open proximal end 173'" of the guide and along rings 52'" of the guide to engage the proximal end of the suture spring device and to push the device further distally within the guide. Pusher 26b'" is advanced by squeezing or compressing handle 86'" or drawing handle 246'" toward finger loop 218b'" of handle 68'". In either case, collar 232'" is moved distally relative to the housing to move flange 74'", and thus pusher 26b'", distally relative to the inner member and the housing. Teeth 240'" have distal faces oriented substantially perpendicular to a longitudinal axis of the applicator and proximal faces disposed at an angle relative to the longitudinal axis in order to permit distal movement or compression of handles 86'" and 246'" while preventing proximal movement thereof. Pusher 26b'" can thus be held in an extended position immediately adjacent the proximal end of suture spring device 38'" by locking member 236'".

To apply the suture spring device to the anatomical tissue, guide 36'" is retracted while maintaining the suture spring device in a substantially stationary position in or in relation to the anatomical tissue. Retraction of guide 36'" is accomplished by releasing locking member 222'" to allow the Ushaped handle 68'" to spring apart, thereby drawing collar 214'" and inner member 28'" proximally while at the same time rotating the inner member to allow guide 36'" to be unthreaded from the suture spring device. As described previously, retraction of guide 36'" causes suture spring device 38'" to no longer be constrained, and allows the suture spring device to contract from the elastically deformed, expanded state toward a relaxed, contracted state to exert a compressive force on the anatomical tissue.

From the above, it will be appreciated that the applicator according to the present invention can be used to position a suture spring device in or in relation to anatomical tissue in an elastically deformed, expanded state so that the suture spring device may then be allowed to move toward a relaxed, contracted state to compress, approximate, occlude, fasten or secure the anatomical tissue. The applicator preferably includes a storage portion for holding at least one suture spring device in a substantially relaxed, contracted state, a guide disposed distally of the storage portion to receive a suture spring device in an elastically deformed, expanded state for positioning in or in relation to anatomical tissue, and a pusher for engaging the suture spring device to permit relative movement between the guide and the suture spring device. The guide can have a tissue penetrating tip as shown, a blunt tip or the distal end of the suture device can be used as a tissue penetrating tip either alone or in combination with the distal end of the guide.

The guide can be used to position any type of suture device in or in relation to anatomical tissue by creating a path in or in relation to the tissue which the suture device will occupy when the guide is removed. Hence, in addition to applying suture devices having an elastic body of coiled configuration, where by "elastic" is meant having an ability to recover an original shape or position after having been deformed and by "coiled" is meant defining a single coil or ring, a portion of a coil or ring or a series of connected coils or rings, the applicator can be used to apply rigid suture devices having substantially the same shape and size as the guide, lengths of filamentary suture material as well as suture devices formed of shape memory alloys, such as nitinol, soft materials which can be hardened by application of energy once applied, or ductile materials, where by "ductile" is meant having a tendency, once bent, to remain in the bent condition. The guide can also be used like a probe to penetrate and dissect anatomical tissue and to supply energy to tissue or devices as required; and, when the guide is used as a probe, instruments such as the grasping instrument shown in FIG. 21 can be used to bring the tissue or device to the probe.

The guide can be made of any suitable medically acceptable material, such as stainless steel, so long as it is configured to have a stiffness suitable for maintaining a suture spring device in an expanded state for positioning in or in relation to anatomical tissue. The guide preferably includes a tubular body of coiled configuration as shown but can also be of straight or angular configuration as desired. When the guide of the applicator is of coiled configuration, the coils can be circular, elliptical, polygonal or have any other curved or angular configuration and, when a guide has more than one coil, adjacent coils can be of the same size and shape or different size and shape depending on the type of procedure to be performed. The tubular body of the guide can have any configuration in transverse cross-section including, but not limited to, circular, elliptical, polygonal and open configurations. Also, the shape of the lumen in transverse cross-section can be different than the shape of the outer surface of the guide in transverse crosssection so that, for example, the outer surface may be circular and the inner surface polygonal or vice versa. Depending upon the manner in which the suture device is moved relative to the guide, the guide can be formed with or without a slot. When formed with a slot, the slot will preferably extend from a proximal end of the guide to a distal end of the guide and will communicate between an exterior surface of the guide and an interior lumen. The slot can have tapered or V-shaped sides to accommodate a ball-shaped knob as shown, or the size of the slot can be straight. Furthermore, although the slot is shown on the outer, convex side of the guide, it can be formed on the inner, concave side or anywhere inbetween or the slot can be made to spiral around the coiled body of the guide. The guide can be concentric with a longitudinal axis of the inner member or offset therefrom.

If an elastic suture spring device is to be applied, an expander can be positioned between the storage portion and the guide to elastically expand the suture spring device in an axial and/or radial direction as it is advanced distally toward the guide. The expander can be a solid surface with a groove or a tubular extension of the guide with or without a slot.

Although the pusher is shown and described herein as including one or more fingers mounted on a tubular body, it will be appreciated that the pusher can have any configuration to engage a suture device including, but not limited to, tubular configurations with fingers biased radially inward at a distal end of the tubular body, tubular configurations with rod-like fingers configured to slide within a hollow, tubular guide and configurations where the body of the pusher is not of tubular configuration. The pusher can be disposed along an exterior or interior of the inner member or a portion of the pusher can be disposed along the exterior and another portion disposed along the interior of the inner member. While the pusher is shown as being spring biased, it will be appreciated that any type of force can be used to move the suture spring device relative to the guide including, but not limited to, mechanical forces provided by springs, magnetic forces and/or hydraulic or pneumatic forces. The pusher can also be made to rotate together with or independently of the suture spring device if desired.

The inner member and drive shaft preferably cooperate to define a central channel through the applicator through which instruments, such as penetrators and graspers can be passed during an operative procedure. Several instruments or implements which can be passed through such a central channel are disclosed in my co-pending application Ser. No. 08/376,186, entitled "Multifunctional Instrument With Interchangeable Operating Units For Performing Endoscopic Procedures," the disclosure of which is incorporated herein by reference. The central channel can also be used for irrigation and aspiration as well as for administering medicaments and fluids to the operative site.

The handle and drive mechanism shown and described herein are exemplary of the types of handles and drive mechanisms suitable for performing the function of moving the inner member and or the suture spring device relative to one another; accordingly, the handle and drive mechanism can have any configuration to produce rotational and/or linear movement of the inner member and/or the suture spring device, including, but not limited to, configurations employing a pair of pivoted legs with finger loops, one fixed and one pivoted leg with finger loops, or resilient U-shaped members connected between outer and inner members of the applicator or between the inner member and the pusher.

Moreover, the handle can have any orientation relative to the longitudinal axis of the applicator including, for example, substantially transverse orientations where the handle extends transversely from a bottom of the housing or substantially longitudinal orientations where the handle extends longitudinally from a rear wall of the housing and is operated like a scissors, or rotatable configurations where the handles can be moved between transverse and longitudinal orientations as desired. While a rack and pinion has been shown for moving the inner member linearly along a longitudinal axis of the applicator, it will be appreciated that any type of force can be used to move the inner member including, but not limited to, mechanical forces provided by rods, pulleys or springs, magnetic forces and/or hydraulic or pneumatic forces.

The components of the applicator can be made of any suitable medical grade materials to permit sterilization for re-use or for single patient use. The components can be made of multiple parts of various configurations and materials to reduce cost. The housing can have various valves and/or seals to control fluid flow and the passage of instruments therethrough, such as the stopcock valve shown at the proximal end of the applicator, and conventional locking mechanisms can be used to hold the trigger within the handle in the fully depressed position or at any other position relative to the handle. In addition, the outer tubular member can be provided with scale markings on an exterior surface to assist the user in determining distances within the body.

It will also be appreciated that rotation of the guide can be combined with linear translation by use of suitable gearing, and that the guide or any other component of the applicator can be configured to rotate in a clockwise or counterclockwise direction when being advanced distally along the longitudinal axis of the applicator depending upon the configuration of the guide or component. Also, the applicator housing can be adapted to allow removal of the inner member from a proximal end of the housing to permit reloading of the inner member without removing the applicator from the operative site. The applicator can also be modified to simply rotate the guide without linear translation or, conversely, to linearly translate the guide without rotation; both modifications requiring manual operations to be performed in order to position the suture device in or in relation to anatomical tissue.

Once the suture device is positioned in or with respect to the tissue, the return of the suture device toward the rest position, can be enhanced, dependent upon the material from which the suture device is constructed, by temperature change and/or by the application of electricity, light or other energy to alter the characteristics of the material.

The features of the various embodiments described above can be combined in any manner desired dependant upon the operational requirements of the procedure to be performed and the complexity of the particular design.

In as much as the present invention is subject to many variations, modifications and changes in detail, it is intended that all subject matter discussed above or shown in the accompanying drawings be interpreted as illustrative only and not be taken in a limiting sense.

What is claimed is:

1. An applicator for applying a suture spring device in or in relation to anatomical tissue, said applicator comprising
   a storage portion configured to hold at least one suture spring device in a substantially relaxed, contracted state;
   a guide disposed distally of said storage portion and including a hollow, tubular body configured to receive therein a suture spring device in an elastically deformed, expanded state for positioning in or in relation to the anatomical tissue; and
   a pusher having a configuration to engage a suture spring device in said guide, said pusher being movable in relation to said guide to control the position of the suture spring device relative to said guide.

2. An applicator as recited in claim 1 and further comprising an expander disposed between said storage portion and said guide to elastically expand the suture spring device as it is moved distally from said storage portion relative to said guide.

3. An applicator as recited in claim 2 wherein said expander includes a solid surface with a groove leading from said storage portion to said guide.

4. An applicator as recited in claim 3 wherein said expander defines a conical surface of increasing diameter in a distal direction and said groove defines a helical path around said conical surface between said storage portion and said guide.

5. An applicator as recited in claim 4 wherein a distal end of said groove communicates with an opening in said guide so that a suture spring device will be loaded into said guide as the device advances distally along said groove.

6. An applicator as recited in claim 1 and further comprising bias means for biasing said pusher distally relative to said guide.

7. An applicator as recited in claim 1 wherein said pusher includes a distal portion slidingly movable through said tubular body of said guide to push a suture spring device distally therein.

8. An applicator as recited in claim 7 wherein said distal portion of said pusher includes a finger formed of a flexible material.

9. An applicator as recited in claim 1 wherein said tubular body of said guide includes a slot communicating between interior and exterior surfaces of said tubular body so that, if the suture spring device includes a knob, the knob can extend laterally through said slot when the suture spring device is disposed within said guide.

10. An applicator as recited in claim 9 wherein a distal end of said pusher includes inwardly biased fingers.

11. An applicator as recited in claim 6 and further comprising a locking mechanism engageable with said pusher to lock said pusher in a retracted position engaging a suture spring device.

12. An applicator as recited in claim 1 wherein an opening is formed in an outer, convex surface of said guide distally of said proximal end of said guide to receive a suture spring device therethrough.

13. An applicator as recited in claim 12 wherein said pusher includes a distal portion movable within said guide to block said opening when advancing a suture spring device through said guide.

14. An applicator as recited in claim 1 and further comprising a drive mechanism coupled with said guide to move said guide relative to a suture spring device engaged by said pusher.

15. An applicator as recited in claim 14 wherein said drive mechanism is operable to move said guide linearly along a longitudinal axis of said guide.

16. An applicator as recited in claim 15 wherein said drive mechanism includes a rotator coupled with said guide to rotate said guide about said longitudinal axis as said guide is moved linearly.

17. An applicator as recited in claim 1 wherein said storage portion, said expander and said guide cooperate to define a central channel through said applicator.

18. An applicator as recited in claim 1 wherein said guide includes an elongate tubular body of coiled configuration.

19. An applicator as recited in claim 1 wherein said tubular body of said guide terminates distally at a tissue penetrating tip.

20. An applicator for applying a suture device in or in relation to anatomical tissue, said applicator comprising a storage portion configured to hold at least one suture device;

a guide disposed distally of said storage portion and including a hollow, tubular body of coiled configuration with an opening to receive therein a suture device; and a pusher having a configuration to engage a suture device in said guide, said pusher being movable in relation to said guide to control the position of the suture device relative to said guide.

21. An applicator as recited in claim 20 and further comprising a drive mechanism coupled with said guide to move said guide relative to the anatomical tissue.

22. An applicator for applying a suture spring device in or in relation to anatomical tissue, said applicator comprising a housing;

an outer tubular member having a proximal end mounted by said housing and terminating distally at a distal end;

an inner member movably disposed in said outer tubular member and including a storage portion configured to hold a suture spring device in a substantially relaxed, contracted state and a guide disposed distally of said storage portion to receive the suture spring device in an elastically deformed, expanded state;

a pusher movably disposed in said outer tubular member to engage the suture spring device so that the position of the suture spring device relative to said guide can be controlled; and a drive mechanism coupled with said inner member to move the inner member relative to said outer tubular member when operated.

23. An applicator as recited in claim 22 wherein said pusher includes a tubular body telescopically received within said outer tubular member and said inner member is received within said tubular body of said pusher.

24. An applicator as recited in claim 23 wherein said inner member is movable between a retracted position where a distal end of said guide is disposed proximally of the distal end of the outer tubular member and an extended position where said distal end of said guide protrudes distally from said outer member.

25. An applicator as recited in claim 24 wherein said pusher is movable distally from a retracted position where a distal end of said pusher engages a suture spring device held by said storage portion when said inner member is in said extended position.

26. An applicator as recited in claim 25 and further comprising a locking mechanism which engages said pusher in said retracted position to prevent distal movement of said pusher so that, when said inner member is moved from said extended position to said retracted position, a suture spring device engaged by said pusher will be loaded into said guide.

27. An applicator as recited in claim 26 and further comprising bias means for biasing said pusher distally relative to said outer tubular member so that said pusher will maintain engagement with a suture spring device loaded in said guide as said guide is moved from said retracted position to said extended position in or in relation to anatomical tissue, said pusher holding the suture spring device substantially stationary in relation to the anatomical tissue when said guide is moved from said extended position back to said retracted position.

28. An applicator as recited in claim 25 and further comprising a handle mounted on said pusher to permit manual movement of said pusher from said extended position to said retracted position.

29. An applicator as recited in claim 22 and further comprising an expander of frustoconical configuration disposed between said storage portion and said guide.

30. An applicator as recited in claim 29 wherein a helical groove is formed in said frustoconical expander to communicate with an opening in said guide.

31. A method of applying a suture spring device in or in relation to anatomical tissue using an applicator having a storage portion and a guide, said method comprising the steps of storing the suture spring device in a substantially relaxed, contracted state within the storage portion of the applicator;

elastically deforming the suture spring device from the relaxed, contracted state to an elastically deformed, expanded state;

holding the suture spring device in the elastically deformed, expanded state within the guide;

positioning the suture spring device in relation to anatomical tissue in the elastically deformed, expanded state using the guide; and removing the guide to allow the suture spring device to move resiliently from the elastically deformed, expanded state toward the relaxed, contracted state to apply a predetermined compressive force to the anatomical tissue.

32. A method of applying a suture spring device as recited in claim 31 wherein said step of holding the suture spring device includes holding the suture spring device substantially stationary and moving the guide relative to the suture spring device to load the device into the guide.

33. A method of applying a suture spring device as recited in claim 32 wherein said step of moving the guide includes moving the guide in a proximal direction relative to the suture spring device.

34. A method of applying a suture spring device as recited in claim 33 wherein said step of moving the guide further includes rotating the guide relative to the suture spring device.

35. A method of applying a suture spring device as recited in claim 31 wherein said step of removing the guide includes holding the suture spring device substantially stationary and moving the guide relative to the suture spring device.

36. A method of applying a suture spring device as recited in claim 35 wherein said step of moving the guide relative to the suture spring device includes moving the guide in a proximal direction relative to the suture spring device.

37. A method of applying a suture spring device as recited in claim 36 wherein said step of moving the guide further includes rotating the guide relative to the suture spring device.

38. A method of applying a suture spring device as recited in claim 37 wherein said step of holding the suture spring device stationary includes positioning a pusher behind the suture spring device to resist movement of the device.

* * * * *